US007160922B2

United States Patent
Bush et al.

(10) Patent No.: US 7,160,922 B2
(45) Date of Patent: Jan. 9, 2007

(54) HEMIHYDRATE OF A SELECTIVE FUNCTIONAL M1 MUSCARINE RECEPTOR AGONIST

(75) Inventors: Julie Kay Bush, Fishers, IN (US); Perry Clark Heath, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/524,960

(22) PCT Filed: Aug. 12, 2003

(86) PCT No.: PCT/US03/23260

§ 371 (c)(1),
(2), (4) Date: Feb. 18, 2005

(87) PCT Pub. No.: WO2004/018411

PCT Pub. Date: Mar. 4, 2004

(65) Prior Publication Data

US 2006/0122280 A1    Jun. 8, 2006

Related U.S. Application Data

(60) Provisional application No. 60/405,443, filed on Aug. 22, 2002.

(51) Int. Cl.
A61K 31/16 (2006.01)
C07C 237/24 (2006.01)

(52) U.S. Cl. ..................................... 514/613; 564/161

(58) Field of Classification Search ................ 514/613; 565/161; 564/161
See application file for complete search history.

(56) References Cited

U.S. PATENT DOCUMENTS

2004/0242584 A1 * 12/2004 Allen et al. ................. 514/247

FOREIGN PATENT DOCUMENTS

WO    WO 03/027061    4/2003

OTHER PUBLICATIONS

Shannon et al. "Xanomeline, an M1/M4 preferring muscarinic cholinergic receptor agonist, produces antipsychotic-like activity in rats and mice" Schizophrenia Research 2000, vol. 42, pp. 249-259.*

* cited by examiner

*Primary Examiner*—Joseph K. McKane
*Assistant Examiner*—Joseph R. Kosack
(74) *Attorney, Agent, or Firm*—Danica Hostettler; Tina M. Tucker

(57) ABSTRACT

The present invention provides crystalline biphenyl-4-carboxylic acid (R)-(6-(1-((4-fluorobenzyl)methylamino)ethylideneamino)-2(R)-hydroxyindan-1-yl)amide hemihydrate, compositions thereof, methods of using the same, processes for making the same, and processes for making intermediates thereof.

6 Claims, No Drawings

HEMIHYDRATE OF A SELECTIVE FUNCTIONAL M1 MUSCARINE RECEPTOR AGONIST

This is the national phase application, under 35 U.S.C. §371, for PCT/US2003/023260 filed on 12 Aug. 2003, which claims the priority of U.S. Provisional Application No. 60/405,443 filed on 22 Aug. 2002.

FIELD OF THE INVENTION

The present invention relates to the field of pharmaceutical and organic chemistry and provides crystalline compounds that are active at the muscarinic receptors.

BACKGROUND OF THE INVENTION

Biphenyl-4-carboxylic acid (R)-(6-(1-((4-fluorobenzyl)methylamino)ethylideneamino)-2(R)-hydroxyindan-1-yl)amide is described in PCT Publication Number WO 03/027061, published Apr. 3, 2003. The forms of the compound described in the above patent application are an anhydrous form and the acetonitrile solvate.

The present invention provides crystalline biphenyl-4-carboxylic acid (R)-(6-(1-((4-fluorobenzyl)methylamino)ethylideneamino)-2(R)-hydroxyindan-1-yl)amide hemihydrate, compositions thereof, methods of using the same, and processes for making the same. The crystalline hemihydrate of the present invention is useful as a selective agonist of the muscarinic M-1 receptor and, as such, is useful for treating a variety of disorders of the central nervous system and other body systems. These disorders include cognitive disorders, ADHD, obesity, Alzheimer's disease, psychoses including schizophrenia, and for alleviation of intraocular pressure such as that found in glaucoma. Because biphenyl-4-carboxylic acid (R)-(6-(1-((4-fluorobenzyl)methylamino)ethylideneamino)-2(R)-hydroxyindan-1-yl)amide is useful for treating disorders associated with muscarinic receptors, there is a need to produce it as a pure, stable, and crystalline form in order to fulfill exacting pharmaceutical requirements and specifications. The novel crystalline hemihydrate of this invention has suitable properties to be conveniently formulated on a commercial scale in, for example, tablets for oral administration, and has suitable processing and storage properties. In particular, the present crystalline hemihydrate is a form that is easy to make in a reproducible and consistent manner. Furthermore, the novel crystalline hemihydrate of this invention exhibits greater thermodynamic stability.

It has been surprisingly discovered that biphenyl-4-carboxylic acid (R)-(6-(1-((4-fluorobenzyl)methylamino)ethylideneamino)-2(R)-hydroxyindan-1-yl)amide can be prepared in a hemihydrate form and having advantageous properties and the manufacturing process for the new form fulfills the desirable features described above.

SUMMARY OF THE INVENTION

The present invention provides biphenyl-4-carboxylic acid (R)-(6-(1-((4-fluorobenzyl)methylamino)ethylideneamino)-2(R)-hydroxyindan-1-yl)amide hemihydrate.

In another embodiment, the present invention provides a pharmaceutical composition comprising biphenyl-4-carboxylic acid (R)-(6-(1-((4-fluorobenzyl)methylamino)ethylideneamino)-2(R)-hydroxyindan-1-yl)amide hemihydrate and a pharmaceutically acceptable diluent.

Because the compounds of the present invention are agonists of the M-1 muscarinic receptor, the compounds of the present invention are useful for the treatment of a variety of disorders associated with muscarinic receptors, including: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia), dementia (including Alzheimer's disease, AIDS-induced dementia, vascular dementia, and dementia lacking distinctive histology), Parkinson's disease, and Huntington's Chorea. Also, the present compounds are useful for treating chronic colitis, including Crohn's disease. Additionally, the present compounds are useful for the treatment of pain (including acute pain and chronic pain), xerostomia (dry mouth), Lewy body disease (including diffuse Lewy body disease), aphasia (including primary aphasia and primary aphasia syndromes), and hypotensive syndromes.

In one of its method aspects, this invention is directed to a method for treating disorders associated with the muscarinic receptors comprising administering to a patient in need thereof an effective amount of biphenyl-4-carboxylic acid (R)-(6-(1-((4-fluorobenzyl)methylamino)ethylideneamino)-2(R)-hydroxyindan-1-yl)amide hemihydrate.

The present invention provides biphenyl-4-carboxylic acid (R)-(6-(1-((4-fluorobenzyl)methylamino)ethylideneamino)-2(R)-hydroxyindan-1-yl)amide hemihydrate for use in therapy. The present invention provides for the use of biphenyl-4-carboxylic acid (R)-(6-(1-((4-fluorobenzyl)methylamino)ethylideneamino)-2(R)-hydroxyindan-1-yl)amide hemihydrate for the manufacture of a medicament for the treatment of disorders associated with muscarinic receptors.

In another embodiment this invention provides a process for making biphenyl-4-carboxylic acid (R)-(6-(1-((4-fluorobenzyl)methylamino)ethylideneamino)-2(R)-hydroxyindan-1-yl)amide hemihydrate.

DETAILED DESCRIPTION OF THE INVENTION

Herein, the Cahn-Prelog-Ingold designations of (R)- and (S)- and the designations of L- and D- for stereochemistry relative to the isomers of glyceraldehyde are used to refer to specific isomers.

The present invention provides biphenyl-4-carboxylic acid (R)-(6-(1-((4-fluorobenzyl)methylamino)ethylideneamino)-2(R)-hydroxyindan-1-yl)amide hemihydrate, and in particular, a crystalline biphenyl-4-carboxylic acid (R)-(6-(1-((4-fluorobenzyl)methylamino)ethylideneamino)-2(R)-hydroxyindan-1-yl)amide hemihydrate.

A number of methods are available to characterize crystalline forms of organic compounds. For example, methods include differential scanning calorimetry, thermogravimetric analysis, solid state NMR spectrometry, infra-red spectroscopy, and X-ray powder diffraction. Among these, X-ray powder diffraction and solid state NMR spectroscopy are very useful for identifying and distinguishing between crystalline forms.

X-ray powder diffraction analysis was performed as follows. Either with or without lightly grinding with an agate mortar and pestle, the dry sample is loaded into a recessed top-loading sample holder and the surface is smoothed with a glass slide. The X-ray powder diffraction patterns were measured using a Siemens D5000 X-ray powder diffractometer equipped with a CuK$_\alpha$ source ($\lambda$=1.54056 Å) operated at 50 kV and 40 mA using divergence slit size of 1 mm, receiving slit of 1 mm, and detector slit of 0.1 mm. Each sample was scanned between 4° and 35° (2θ) with a step size of 0.02° and a maximum scan rate of 3 sec/step. Data is collected using a Kevex solid-state silicon lithium detector. Optimally, a silicon standard is run routinely to check the instrument alignment.

It is well known in the crystallography art that, for any given crystal form, the relative intensities and peak widths of the diffraction peaks may vary due to a number of factors, including the effects of preferred orientation and/or particle size. Where the effects of preferred orientation and/or particle size are present, peak intensities may be altered, but the characteristic peak positions of the polymorph are unchanged. See, e.g., The United States Pharmacopoeia #24, National Formulary #19, pages 1843–1844, 2000. Furthermore, it is also well known in the crystallography art that, for any given crystal form, the angular peak positions may vary slightly. For example, peak positions can shift due to sample displacement or a variation in the temperature or relative humidity at which a sample is analyzed. In the present case, a peak position variability of ±0.10° in 2θ will take into account these potential variations without hindering the unequivocal identification of the crystalline form of the present invention.

The angular peak positions in 2θ and corresponding relative intensity data for all peaks with intensities equal to or greater than 5 to 10% of the largest peak for biphenyl-4-carboxylic acid (R)-(6-(1-((4-fluorobenzyl)methylamino)ethylideneamino)-2(R)-hydroxyindan-1-yl)amide hemihydrate are listed in Table 1.

Peak position was obtained in 2θ values and peak intensities for the most prominent features (relative intensities greater than 5 to 10%) were measured using a double-derivative peak picking method.

Accordingly, the present invention includes the particular crystal biphenyl-4-carboxylic acid (R)-(6-(1-((4-fluorobenzyl)methylamino)ethylideneamino)-2(R)-hydroxyindan-1-yl)amide hemihydrate characterized by the angular peak positions in 2θ and corresponding relative intensity data in Table 1, which lists the 2θ values and relative intensities greater than 5 to 10% using the methodology described above with CuK$_\alpha$ radiation:

TABLE 1

| Unground | | 5 min grinding | |
|---|---|---|---|
| 2θ (°) | I$_o$/I$_{100}$(%) | 2θ (°) | I$_o$/I$_{100}$(%) |
| 5.2 | 17.1 | 5.2 | 16.2 |
| 6.2 | 8.0 | 6.2 | 10.6 |
| 12.6 | 100 | 12.6 | 100 |
| 14.0 | 23.7 | 13.9 | 20.3 |
| 14.4 | 15.8 | 14.5 | 12.6 |
| 14.9 | 12.2 | 14.9 | 10.8 |
| 15.6 | 39.1 | 15.6 | 37.0 |
| 17.0 | 29.0 | 16.9 | 26.2 |
| 18.8 | 49.9 | 18.8 | 58.6 |
| 19.6 | 29.8 | | |
| 20.0 | 52.2 | 20.0 | 91.6 |
| 20.9 | 7.7 | 20.9 | 13.5 |
| 21.7 | 5.7 | 21.7 | 13.7 |
| 22.6 | 30.4 | 22.6 | 52.1 |
| 23.3 | 15.9 | 23.2 | 21.1 |
| 25.9 | 14.1 | 25.9 | 20.0 |
| 26.5 | 9.4 | 26.4 | 12.3 |
| 27.5 | 5.4 | 27.4 | 6.5 |

The intensities of the sample ground for 5 minutes are representative of the diffraction pattern where attempts were made to minimize the effects of preferred orientation and/or particle size. It should also be noted that the computer-generated numbers are listed in this table.

Thus, a properly prepared crystalline sample of biphenyl-4-carboxylic acid (R)-(6-(1-((4-fluorobenzyl)methylamino)ethylideneamino)-2(R)-hydroxyindan-1-yl)amide hemihydrate may be characterized by X-ray diffraction pattern in 2θ values using CuK$_\alpha$ radiation having peaks as described in Table 1, and in particular having a peak at 5.2, 6.2, 12.6, 14.0, 15.6, 17.0, 18.8, 19.6, 20.0, or 22.6; more particularly having a peak at 5.2, 6.2, 12.6, 15.6, 18.8, or 20.0; peaks at any two of 5.2, 6.2, 12.6, 15.6, 18.8, and 20.0; or having peaks at 5.2, 6.2, 12.6, 14.0, 15.6, 17.0, 18.8, 19.6, 20.0, and 22.6.

Crystalline biphenyl-4-carboxylic acid (R)-(6-(1-((4-fluorobenzyl)methylamino)ethylideneamino)-2(R)-hydroxyindan-1-yl)amide hemihydrate may also be characterized by solid state NMR spectroscopy. Solid state $^{13}$C chemical shifts reflect not only the molecular structure of but also the electronic environment of the molecule in the crystal.

Solid state NMR ($^{13}$C) spectroscopy can be carried out using $^{13}$C cross polarization/magic angle spinning (CP/MAS). NMR (solid-state NMR or SSNMR) spectrum was obtained using a Varian Unity Inova 400 MHz spectrometer operating at a carbon frequency of 100.573 MHz, equipped with a complete solids accessory and a Chemagnetics 4.0 mm T3 probe. Acquisition parameters were as follows: 90° proton r.f. pulse width 4.0 μs, contact time 2.0 ms, pulse repetition time 10 s, MAS frequency 10.0 kHz, spectral width 50 kHz, and acquisition time 50 ms. Chemical shifts were referenced externally to the methyl group of hexamethylbenzene (δ=17.3 ppm), that is, by sample replacement with hexamethylbenzene.

The spectrum for biphenyl-4-carboxylic acid (R)-(6-(1-((4-fluorobenzyl)methylamino)ethylideneamino)-2(R)-hydroxyindan-1-yl)amide hemihydrate comprises isotropic peaks at the following chemical shifts: 15.4, 17.8, 35.3, 38.1, 39.3, 40.2, 54.1, 63.4, 81.6, 84.7, 116.9, 118.1, 120.2, 121.5, 124.7, 126.7, 129.0, 131.9, 133.0, 134.0, 135.0, 136.7, 137.5, 140.4, 141.7, 143.9, 151.6, 154.5, 156.8, 160.4, 162.2, 162.9, 164.6, and 169.8 ppm.

In another embodiment this invention provides a process for making biphenyl-4-carboxylic acid (R)-(6-(1-((4-fluorobenzyl)methylamino)ethylideneamino)-2(R)-hydroxyindan-1-yl)amide hemihydrate comprising crystallizing biphenyl-4-carboxylic acid (R)-(6-(1-((4-fluorobenzyl)methylamino)ethylideneamino)-2(R)-hydroxyindan-1-yl)amide from a suitable solvent under conditions which yield biphenyl-4-carboxylic acid (R)-(6-(1-((4-fluorobenzyl)methylamino)ethylideneamino)-2(R)-hydroxyindan-1-yl)amide hemihydrate.

The precise conditions under which biphenyl-4-carboxylic acid (R)-(6-(1-((4-fluorobenzyl)methylamino)ethylideneamino)-2(R)-hydroxyindan-1-yl)amide hemihydrate is formed may be empirically determined and it is only possible to give a number of methods which have been found to be suitable in practice.

Thus, for example, biphenyl-4-carboxylic acid (R)-(6-(1-((4-fluorobenzyl)methylamino)ethylideneamino)-2(R)-hydroxyindan-1-yl)amide hemihydrate may be prepared by crystallization under controlled conditions. Crystallization from a solution and slurrying techniques are contemplated to be within the scope of the present process. In particular, the hemihydrate of the present invention can be prepared by crystallization from an aqueous-alcohol solvent mixture, including methanol-water, ethanol-water, isopropanol-water, methanol-isopropanol/water, and methanol-acetonitrile/ water. A suitable solvent is one that is capable of containing sufficient water, at the concentrations used, to form the present hemihydrate. In practice, it has been found that methanol-water is preferred.

The use of an anti-solvent may be advantageous. As used in the context of the present process, the term "anti-solvent" refers to a solvent in which biphenyl-4-carboxylic acid (R)-(6-(1-((4-fluorobenzyl)methylamino)ethylideneamino)-2(R)-hydroxyindan-1-yl)amide hemihydrate is significantly less soluble relative to the selected solvent. Preferably, when an anti-solvent is used it is miscible with the selected solvent.

A crystallization is generally carried out by dissolving biphenyl-4-carboxylic acid (R)-(6-(1-((4-fluorobenzyl)methylamino)ethylideneamino)-2(R)-hydroxyindan-1-yl) amide hemihydrate in an organic solvent and adding an anti-solvent, for example, water, to give a solid. In particular, slow anti-solvent addition of water to an alcoholic solution of the compound between ambient and 60° C. is the preferred method of crystallization. Elevated temperatures for excessive periods of time can cause hydrolysis in aqueous media; thus, lower temperatures are preferred. Seeding may be advantageous. Preferably the crystallization solution is cooled slowly. The crystallization is most conveniently cooled to temperatures of ambient temperature to about 0° C.

The present invention is further illustrated by the following examples and preparations. These examples and preparations are illustrative only and are not intended to limit the invention in any way.

The terms used in the examples and preparations have their normal meanings unless otherwise designated. For example, "° C." refers to degrees Celsius; "M" refers to molar or molarity; "mmol" refers to millimole or millimoles; "g" refers to gram or grams; "mL" refers milliliter or milliliters; "mp" refers to melting point; "brine" refers to a saturated aqueous sodium chloride solution; etc. In the $^1$H NMR, all chemical shifts are given in δ, unless otherwise indicated.

EXAMPLE 1-1

Biphenyl-4-carboxylic acid (R)-(6-(1-((4-fluorobenzyl)methylamino)ethylideneamino)-2(R)-hydroxyindan-1-yl)amide

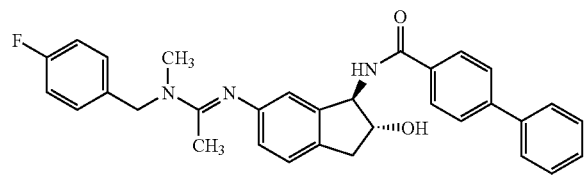

Slowly add a solution of 375 g (5.13 mol, 112 equiv) of N-methylacetamide in THF (1.76 L) to 224 g (5.55 mol, 1.2 equiv) of sodium hydride (60% dispersion in mineral oil) as a slurry in THF (8.75 L). After 30 minutes when 25% of the solution has been added, add 875 g (4.63 mole, 1 equiv) of 4-fluorobenzylbromide and the remaining N-methylacetamide and 4-fluorobenzylbromide solutions concurrently over the next 3 h. Use a water bath to maintain the temperature below 40° C. Stir the resulting mixture overnight and pour into a mixture of 20% NH$_4$Cl (2.5 L), water (6.5 L), and ethyl acetate (9 L). Separate the layers and back-extract the aqueous layer with ethyl acetate (4.5 L, then 2 L). Combine the organic layers and wash with water (4 L) and then brine (7 L). Dry the organic layer (Na$_2$SO$_4$) and remove the solvent to afford a residue. Dissolve the residue in acetonitrile (7 L) and heptane (1.75 L). Separate the layers and wash the acetonitrile layer again with heptane (1.75 L). Combine the heptane layers and back-extract with acetonitrile (0.5 L). Combine the acetonitrile layers and evaporate to afford 0.814 kg of N-methyl-N-(4-fluorobenzyl)acetamide.

Dissolve N-methyl-N-(4-fluorobenzyl)acetamide (0.500 kg, 2.76 mol) in THF (11.5 L). Add phosphorus pentasulfide (0.737 kg, 1.65 mol, 0.6 equiv) and heat the mixture to reflux over 1–2 hours. After 5 h at reflux, allow the mixture to cool to room temperature, filter off the solids, and wash with 12.5 L of THF. Combine the filtrate with an identical filtrate from a separate reaction and concentrate to 0.978 kg of a residue. Dissolve the residue and chromatograph on 2.7 kg of silica gel using CH$_2$Cl$_2$ to afford 1.01 kg of solid. Slurry the solid with methylene chloride (1 L) for 15–30 min, add heptane (5 L), cool the mixture to 0–5° C., and stir for 2 h. Collect the solid by filtration and dry to afford 0.814 kg of N-methyl-N-(4-fluorobenzyl)thioacetamide.

Add 11.5 L of acetonitrile and 2.52 kg (17.7 mol, 1.5 equiv) of methyl iodide to 2.30 kg (11.6 mol) of N-methyl-N-(4-fluorobenzyl)acetamide. Heat the mixture to 35° C. for 21 h. Reduce the volume by half on a rotary evaporator and add 14 L of MTBE. Reduce the volume again by half and add another 14 L of MTBE. Cool the resulting slurry to 0° C., collect the solid by filtration, and dry to afford 3.92 kg of 1-methylthio-1-methyl-N-(4-fluorobenzyl)-N-methylimmonium iodide as a white solid.

Add 85 L of concentrated NH$_4$OH and 28 L of water to 6.20 kg (35.0 mol) of 1,2-epoxy-6-nitroindane. Heat the mixture at 36° C. for 21 h and allow to cool to room temperature. Filter the reaction mixture over a bed of wet Celite (10 kg) and rinse the cake with water. To a wet filter cake of (1R,2R)-1-amino-6-nitroindan-2-ol prepared from 6.20 Add to the wet cake 155 L of methanol, 1.3 L of water, and 5.80 kg (38.1 mol, 1.09 equiv) of (S)-(+)-mandelic acid. Heat the mixture for 2 h at 55° C. and filter through a carbon impregnated filter cartridge. Reduce the filtrate volume by vacuum distillation to about 35 L and add 130 L of EtOAc. Reduce the volume by vacuum distillation to about 65 L. Cool the mixture to −8° C. and stir for 8 h. Filter the slurry and dry the solid to afford 7.6 kg of a solid. Slurry this solid in 30 L of methanol and 0.3 L of water, and heat the mixture at reflux for 0.5 h. Cool the mixture to 45° C. over 0.5 h and stir for 12 h, followed by cooling to 22° C. and stirring for 10 h. Collect the solid by filtration and dry to afford 2.7 kg of (1R,2R)-1-amino-6-nitroindan-2-ol (S)-mandelate.

Add (1R,2R)-1-amino-6-nitroindan-2-ol mandelate (0.64 kg, 1.85 mol) to a mixture of toluene (9.6 L) and aqueous 1 N NaOH (4.8 L, 4.8 mol, 2.6 equiv). After 1 h, add 4-biphenylcarbonyl chloride (0.44 kg, 2.0 mol, 1.1 equiv) in portions over 20–30 min. After 22 hours, filter the solids under vacuum and rinse sequentially with 0.5 L of toluene, 2 L of water, and 2 L of toluene. Dry the cake to afford 0.74 kg of biphenyl-4-carboxylic acid (R)-(6-nitro-2-hydroxyindan-1-yl)amide. Add 38.2 L of ethyl acetate to 1.914 kg of biphenyl-4-carboxylic acid (R)-(6-nitro-2(R)-hydroxyindan-1-yl)amide prepared in a similar manner. Stir the slurry for 18 h, collect the solid by filtration, dry to afford 1.76 kg of biphenyl-4-carboxylic acid (R)-(6-nitro-2(R)-hydroxyindan-1-yl)amide as a white solid.

Combine a slurry of 0.176 kg of 10% Pd—C (50% water wet) and 1.7 kg of biphenyl-4-carboxylic acid (R)-(6-nitro- 2(R)-hydroxyindan-1-yl)amide in 17.5 L of DMF with hydrogen (50 psi, 345 kPa). After 19 h, filter the reaction mixture, add a portion of the DMF solution (5 L) to water (10 L), and stir the slurry for 2 h—repeat twice to work up the entire reaction volume. Filter the slurries together, and wash the resulting filter cake with water (3×7 L). Dry the filter cake to afford 1.42 kg of biphenyl-4-carboxylic acid (R)-(6-amino-2(R)-hydroxyindan-1-yl)amide.

Slurry biphenyl-4-carboxylic acid (R)-(6-amino-2(R)-hydroxyindan-1-yl)amide (0.969 kg, 2.81 mol) in THF (9.7 L) and add 1-methylthio-1-methyl-N-(4-fluorobenzyl)-N-methylimmonium iodide (0.954 kg, 2.81 mol) and 4-dimethylaminopyridine (34.5 g, 0.281). Stir the mixture for 24 h, and remove the solvent in vacuo. Dissolve the resulting foam in $CH_2Cl_2$ (12.5 L) and wash the organic phase with 1.0 N HCl (1×4 L and 1×3 L), 1.0 M NaOH (1×2.4 L) and saturated NaCl (1×4 L). Separate the organic phase, dry ($Na_2SO_4$), filter, and remove the solvent to yield a solid. Dissolve the solid in acetonitrile (9 L) while heating to 35–40° C. After approximately 30 minutes, add seed crystals, which results in a thick, white slurry. Cool the mixture to −15° C. and stir at this temperature for 1–2 h. Filter the slurry and dry to provide 1.10 kg of the title compound as a partial acetonitrile solvate.

$^1$H NMR (CDCl$_3$): δ 7.90 (d, 2, J=8.6), 7.69 (d, 2, J=8.6), 7.63 (d, 2, J=8.2), 7.48 (t, 2, J=8.2, 7.6), 7.41 (d, 1, J=7.3), 7.24 (dd, 2, J=8.5, 5.2), 7.14 (d, 1, J=7.9), 7.04 (t, 2, J=8.7), 6.72–6.63 (m, 3), 5.31 (t, 1, J=5.6), 4.84 (br s, 1), 4.64 (dd, 2, J=21.4, 15.6), 4.54 (dd, 1, J=14.0, 7.9), 3.32 (dd, 1, J=15.6, 7.9), 3.01 (s, 3), 2.95 (dd, 1, J=15.7, 8.0), 1.97 (s, 3). MS (m/z): 508.2 (M+1).

EXAMPLE P-1

Biphenyl-4-carboxylic acid (R)-(6-(1-((4-fluorobenzyl)methylamino)ethylideneamino)-2(R)-hydroxyindan-1-yl)amide hemihydrate Add 21.8 L of methanol to 2.86 kg of biphenyl-4-carboxylic acid (R)-(6-(1-((4-fluorobenzyl)methylamino)ethylideneamino)-2(R)-hydroxyindan-1-yl)amide acetonitrile solvate. Pass the solution through a carbon impregnated filter and rinse the filter with 24 L of methanol. Add 5.7 kg of water to the solution over 35 min followed by 15 g of biphenyl-4-carboxylic acid (R)-(6-(1-((4-fluorobenzyl)methylamino)ethylideneamino)-2(R)-hydroxyindan-1-yl)amide hemihydrate seed crystals. After 20 min, add 1.15 kg of water followed by 15 g of seed crystals. After 1 h, add another 1.15 kg of water over 30 min followed by 15 g of seed crystals. After 10 min, add 3.4 kg of water over 1 h and stir the slurry at room temperature for 1 h and at 0° C. for 45 min. Collect the solid by filtration, rinse with a cold solution of 11.4 L of methanol and 2.9 L of water, and dry to afford 2.19 kg of the title compound as a white solid.

Additionally, one of ordinary skill in the art will recognize that two alternate names for this crystalline compound are [1,1'-biphenyl]-4-carboxamide N-[(1R,2R)-6-[[1-[[(4fluorophenyl)methyl]methylamino]ethylidene]amino]-2,3-dihydro-2-hydroxy-1H-inden-1-yl]-, hydrate (2:1) and 6-(1-((4-fluorobenzyl)methylamino)ethylideneamino)-2-hydroxy-1-biphenylamidoindane hemihydrate.

EXAMPLE P-2

Biphenyl-4-carboxylic acid (R)-(6-(1-((4-fluorobenzyl)methylamino)ethylideneamino)-2(R)-hydroxyindan-1-yl)amide hemihydrate Dissolve biphenyl-4-carboxylic acid (R)-(6-(1-((4-fluorobenzyl)methylamino)ethylideneamino)-2(R)-hydroxyindan-1-yl)amide acetonitrile solvate (2.0 g) in methanol (24 mL) at 20–23° C. Add water (5 mL) to the solution, followed by hemihydrate seed crystals (20 mg). Stir the mixture for 2 h at 20–23° C., then cool to 0–5° C. Filter the mixture, wash with a solution of methanol (8 mL) and water (2 mL), and dry at 50–60° C. under vacuum for 16 h to give 1.66 g of the title compound.

EXAMPLE P-3

Biphenyl-4-carboxylic acid (R)-(6-(1-((4-fluorobenzyl)methylamino)ethylideneamino)-2(R)-hydroxyindan-1-yl)amide hemihydrate Combine a solution of 6-(1-((4-fluorobenzyl)methylamino)ethylideneamino)-2-hydroxy-1-biphenylaminoindane acetonitrile solvate (101 g) and methanol (1.2 L) with Darco G-60 (5 g). After stirring for 15–30 min at 15–25° C., filter the mixture and rinse the filtered solids with methanol (0.4 L). Add water (0.4 L) to the combined filtrate, rinse, and add hemihydrate seed crystals (1.5 g). Stir the mixture 2–3 h at 15–25° C., then cool to 0–5° C. and stir another 90 min. Filter the mixture, wash with a 0–5° C. solution of methanol (0.8 L) and water (0.2 L), and dry at 47–53° C. under vacuum for 20 h to give 88.7 g of the title compound.

The compounds of the present invention can be administered alone or in the form of a pharmaceutical composition, that is, combined with pharmaceutically acceptable carriers or excipients, the proportion and nature of which are determined by the solubility and chemical properties of the compound selected, the chosen route of administration, and standard pharmaceutical practice. The compounds of the present invention, while effective themselves, may be formulated and administered in the form of their pharmaceutically acceptable salts, for purposes of stability, convenience, solubility, and the like. In practice, the compounds of the present invention are usually administered in the form of pharmaceutical compositions, that is, in admixture with pharmaceutically acceptable carriers or diluents.

Thus, the present invention provides pharmaceutical compositions comprising a compound of the present invention and a pharmaceutically acceptable diluent. The present invention also provides suitable packaging, including a label, containing the pharmaceutical compositions comprising a compound of the present invention.

The compounds of the present invention can be administered by a variety of routes. In effecting treatment of a patient afflicted with disorders described herein, a compound of the present invention can be administered in any form or mode which makes the compound bioavailable in an effective amount, including oral and parenteral routes. For example, compounds of the present invention can be administered orally, by inhalation, subcutaneously, intramuscularly, intravenously, transdermally, intranasally, rectally, occularly, topically, sublingually, buccally, and the like. Oral administration is generally preferred for treatment of the disorders described herein.

One skilled in the art of preparing formulations can readily select the proper form and mode of administration depending upon the particular characteristics of the compound selected, the disorder or condition to be treated, the stage of the disorder or condition, and other relevant circumstances. (*Remington's Pharmaceutical Sciences,* 18th Edition, Mack Publishing Co. (1990)).

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, inhalation, parenteral, or topical use and may be administered to the patient in the form of tablets, capsules, aerosols, inhalants, suppositories, solutions, suspensions, or the like.

The compounds of the present invention may be administered orally, for example, with an inert diluent or capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the present invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention may be determined by a person skilled in the art.

The tablets, pills, capsules, troches, and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of oral and parenteral therapeutic administration, the compounds of the present invention may be incorporated into a solution or suspension. These preparations typically contain at least 0.1% of a compound of the invention, but may be varied to be between 0.1 and about 90% of the weight thereof. The amount of the compound of the present invention present in such compositions is such that a suitable dosage will be obtained. The solutions or suspensions may also include one or more of the following adjuvants: sterile diluents such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Preferred compositions and preparations are able to be determined by one skilled in the art.

The compounds of the present invention may also be administered topically, and when done so the carrier may suitably comprise a solution, ointment, or gel base. The base, for example, may comprise one or more of the following: petrolatum, lanolin, polyethylene glycols, bees wax, mineral oil, diluents such as water and alcohol, and emulsifiers, and stabilizers. Topical formulations may contain a concentration of the compound of the present invention or its pharmaceutical salt from about 0.1 to about 10% w/v (weight per unit volume).

The compounds of the present invention are agonists of the M-1 muscarinic receptors. Moreover the compounds of the present invention are selective agonists of that particular muscarinic receptor. The compounds of the present invention possess particularly useful properties related to their bioavailability, pharmacokinetics, safety, and efficacy. Muscarinic agonists, including their subtype binding profile, can be identified by the methods that are well known in the art.

In one embodiment, the present invention provides methods of treating disorders associated with muscarinic receptors, comprising: administering to a patient in need thereof an effective amount of a compound of the present invention. Thus, the present invention contemplates the various disorders described to be treated herein and others which can be treated by such agonists as are appreciated by those skilled in the art.

A number of the disorders which can be treated by muscarinic agonists are known according to established and accepted classifications, while others are not. For example, cognition is a complicated and sometimes poorly defined phenomenon. It is, however, widely recognized that cognition includes various "domains." These domains include short term memory, long term memory, working memory, executive function, and attention.

It is understood that the compounds of the present invention are useful for treatment of disorders characterized by a deficit in any of the cognitive domains listed above or in other aspects of cognition. Thus the term "cognitive disorders" is meant to encompass any disorder characterized by a deficit in one or more cognitive domain, including but not limited to short term memory, long term memory, working memory, executive function, and attention.

One cognitive disorder to be treated by the present invention is age-related cognitive decline. This disorder is not well defined in the art, but includes decline in the cognitive domains, particularly the memory and attention domains, which accompany aging. Another cognitive disorder is mild cognitive impairment. Again, this disorder is not well defined in the art, but involves decline in the cognitive domains, and is believed to represent a group of patients the majority of which have incipient Alzheimer's disease. Another cognitive disorder is cognitive impairment associated with schizophrenia. The relationship between cognitive disturbances and other symptoms of schizophrenia is not clearly understood at present. It has been observed that some people experience cognitive problems much before they develop positive symptoms, while others acquire cognitive deterioration after the first episode and with subsequent relapses. Yet another cognitive disorder is chemotherapy-induced cognitive impairment. People who undergo cancer chemotherapy may experience a decline in cognitive function and this decline can be long lasting. Also, a wide variety of insults, including stroke, ischemia, hypoxia, inflammation, infectious processes and cognitive deficits subsequent to cardiac bypass surgery and grafting, stroke, cerebral ischemia, spinal cord trauma, head trauma, perinatal hypoxia, fetal alcohol syndrome, cardiac arrest, and hypoglycemic neuronal damage, vascular dementia, multi-infarct dementia, amylotrophic lateral sclerosis, chemotherapy, and multiple sclerosis can result in cognitive deficits as a sequella which can be treated according to the present invention.

Where the disorders which can be treated by muscarinic agonists are known according to established and accepted classifications, these classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

In particularly preferred embodiments, the present invention provides methods of treating disorders selected from the group consisting of: cognitive disorders (including age-related cognitive disorder, mild cognitive impairment, cognitive impairment associated with schizophrenia, and chemotherapy-induced cognitive impairment), ADHD, mood disorders (including depression, mania, bipolar disorders), psychosis (in particular schizophrenia and schizophreniform disorder), dementia (including Alzheimer's disease, AIDS-induced dementia, vascular dementia, and dementia lacking distinctive histology), Parkinson's disease, Huntington's Chorea, pain (including acute pain and chronic pain), xerostomia (dry mouth), Lewy body disease (including diffuse Lewy body disease), aphasia (including primary aphasia and primary aphasia syndromes), aphasia (including primary aphasia and primary aphasia syndromes), hypotensive syndromes, and chronic colitis (including Crohn's disease), comprising: administering to a patient in need thereof an effective amount of a compound of the present invention. That is, the present invention provides for the use of a compound of the present invention or pharmaceutical composition thereof for the treatment disorders associated with muscarinic receptors.

It is recognized that the terms "treatment" and "treating" are intended to include improvement of the symptomatology associated with each of the disorders associated with muscarinic receptors described herein. Also, it is also recognized that one skilled in the art may affect the disorders by treating a patient presently afflicted with the disorders or by prophylactically treating a patient believed to be susceptible to such disorders with an effective amount of the compound of the present invention. Thus, the terms "treatment" and "treating" are intended to refer to all processes wherein there may be a slowing, interrupting, arresting, controlling, or stopping of the progression of the disorders described herein, but does not necessarily indicate a total elimination of all symptoms, and is intended to include prophylactic treatment of such disorders.

It is understood that the present invention includes adjunctive treatment of the disorders described herein. More specifically, the compounds of the present invention are useful to treat disorders in which a cognitive deficit is one of the symptoms in combination with a wide variety of other therapeutic agents, in particular, in combination with AMPA potentiators; with typical and atypical antipsychotics, including olanzapine; with a variety of agents such as mGluR agonists, with NMDA antagonists, with IL 1–6 inhibitors, with other cholinergics, including cholinesterase inhibitors, such as tacrine and donepezil, and compounds that inhibit amyloid protein processing, including inhibitors of amyloid precursor protein processing and antibodies directed against amyloid proteins; with antidepressants, including SSRIs and SNRIs such as fluoxetine, paroxetine, and venlafaxine; and with anxiolytic agents; etc. It is believed that the combinations above are synergistically beneficial providing efficacy at doses that are a small fraction of those required to produce the same effect with the individual components.

In accordance with the adjunctive treatments described above, the present invention also provides a product containing a compound of the present invention and one or more therapeutic agents selected from the group consisting of AMPA potentiators; typical and atypical antipsychotics, including olanzapine; mGluR agonists; NMDA antagonists; IL 1–6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents as a combined preparation for simultaneous, separate or sequential administration in the treatment of disorders in which a cognitive deficit is one of the symptoms. In another embodiment the present invention also provides for the use of a compound of the present invention together with one or more therapeutic agents selected from AMPA potentiators; typical and atypical antipsychotics, including olanzapine; mGluR agonists; NMDA antagonists; IL 1–6 inhibitors; cholinesterase inhibitors, such as tacrine and donepezil; compounds that inhibit amyloid protein processing, including inhibitors of amyloid precursor protein processing and antibodies directed against amyloid proteins; antidepressants, including SSRIs and SNRIs such as fluoxetine, paroxetine, and venlafaxine; and anxiolytic agents for the manufacture of a medicament as a combined preparation for simultaneous, separate or sequential administration in the treatment of disorders in which a cognitive deficit is one of the symptoms.

As used herein, the term "patient" includes a mammal which is afflicted with one or more disorders associated with muscarinic receptors. It is understood that guinea pigs, dogs, cats, rats, mice, horses, cattle, sheep, pigs, and humans are examples of animals within the scope of the meaning of the term.

As used herein, the term "effective amount" of a compound of the present invention refers to an amount, that is, the dosage which is effective in treating the disorders described herein.

An effective amount can be readily determined by the attending diagnostician, as one skilled in the art, by the use of conventional techniques and by observing results obtained under analogous circumstances. In determining an effective amount, the dose of a compound of the present invention, a number of factors are considered by the attending diagnostician, including, but not limited to: the compound of the present invention to be administered; the co-administration of other therapies, if used; the species of mammal; its size, age, and general health; the specific disorder involved; the degree of involvement or the severity of the disorder; the response of the individual patient; the mode of administration; the bioavailability characteristics of the preparation administered; the dose regimen selected; the use of other concomitant medication; and other relevant circumstances.

An effective amount of a compound of the present invention is expected to vary from about 0.01 milligram per kilogram of body weight per day (mg/kg/day) to about 50 mg/kg/day, and preferable from 0.1 milligram per kilogram of body weight per day (mg/kg/day) to about 20 mg/kg/day. More preferred amounts can be determined by one skilled in the art.

Of the disorders to be treated according to the present invention a number are particularly preferred. Particularly preferred disorders include the treatment of cognitive disorders (particularly mild cognitive impairment and cognitive impairment associated with schizophrenia), Alzheimer's disease, and psychosis, including schizophrenia.

A number of preclinical laboratory in vitro and in vivo models have been described for the disorders described herein.

What is claimed is:

1. A crystalline biphenyl-4-carboxylic acid (R)-(6-(1-((4-fluorobenzyl)methylamino]ethylideneamino)-2(R)-hydroxyindan-1-yl)amide hemihydrate characterized by the X-ray powder diffraction pattern comprising peaks at 5.2 and 6.2 (±0.1° 2θ).

2. A crystalline biphenyl-4-carboxylic acid (R)-(6-(1-((4-fluorobenzyl)methylamino]ethylideneamino)-2(R)-hydroxyindan-1-yl)amide hemihydrate characterized by the X-ray powder diffraction pattern comprising peaks at 15.6 and 18.8 (±0.1° 2θ).

3. A crystalline biphenyl-4-carboxylic acid (R)-(6-(1-((4-fluorobenzyl)methylamino]ethylideneamino)-2(R)-hydroxyindan-1-yl)amide hemihydrate characterized by the X-ray powder diffraction pattern comprising peaks at 5.2, 6.2, 12.6, 15.6, 18.8, and 20.0 (±0.10° 2θ).

4. A crystalline biphenyl-4-carboxylic acid (R)-(6-(1-((4-fluorobenzyl)methylamino]ethylideneamino)-2(R)-hydroxyindan-1-yl)amide hemihydrate characterized by the X-ray powder diffraction pattern comprising peaks at 5.2, 6.2, 12.6, 14.0, 15.6, 17.0, 18.8, 19.6, 20.0, and 22.6 (±0.10° 2θ).

5. A method of treating Alzheimer's disease comprising administering to a patient in need thereof an effective amount of the biphenyl-4-carboxylic acid (R)-(6-(1-((4-fluorobenzyl)methylamino]-ethylideneamino)-2(R)-hydroxyindan-1-yl)amide hemihydrate of any one of claims 1–4.

6. A method of treating schizophrenia comprising administering to a patient in need thereof an effective amount of the biphenyl-4-carboxylic acid (R)-(6-(1-((4-fluorobenzyl)methylaminolethylideneamino)-2(R)-hydroxyindan-1-yl)amide hemihydrate of any one of claims 1–4.

* * * * *